United States Patent
Rhodes

(10) Patent No.: US 9,032,960 B2
(45) Date of Patent: May 19, 2015

(54) MALE CONDOM SKIN DRESSING

(71) Applicant: Anthony D Rhodes, Glen Ellyn, IL (US)

(72) Inventor: Anthony D Rhodes, Glen Ellyn, IL (US)

(*) Notice: Subject to any disclaimer, the term of this patent is extended or adjusted under 35 U.S.C. 154(b) by 0 days.

(21) Appl. No.: 13/622,886

(22) Filed: Sep. 19, 2012

(65) Prior Publication Data
US 2014/0076329 A1 Mar. 20, 2014

(51) Int. Cl.
*A61F 6/04* (2006.01)

(52) U.S. Cl.
CPC .............. *A61F 6/04* (2013.01); *A61F 2006/047* (2013.01)

(58) Field of Classification Search
USPC ........... 128/842, 844, 918; 604/349, 351–353
See application file for complete search history.

(56) References Cited

U.S. PATENT DOCUMENTS

| | | | |
|---|---|---|---|
| 5,102,405 A | 4/1992 | Conway et al. | |
| 5,496,605 A * | 3/1996 | Augst et al. | 428/43 |
| 5,758,659 A * | 6/1998 | Thompson | 128/844 |
| 6,209,543 B1 * | 4/2001 | Star | 128/844 |
| 7,963,285 B2 * | 6/2011 | Attila | 128/844 |
| 2005/0150502 A1 * | 7/2005 | Ayres | 128/844 |
| 2008/0312574 A1 | 12/2008 | Pernot | |

OTHER PUBLICATIONS

Nexcare 3M, Tegaderm; waterproof transparent dressing.

* cited by examiner

*Primary Examiner* — Patricia Bianco
*Assistant Examiner* — Keri J Nelson
(74) *Attorney, Agent, or Firm* — Michael P. Mazza, LLC

(57) ABSTRACT

A male condom skin dressing, a kit, and a method of using it. The skin dressing may include a waterproof, generally conically-shaped shell having a base portion and a tip portion, and securing material circumferentially wrapped around at least the base portion of the shell to aid in releasably securing the shell. The securing material may be flexible adhesive strips or elastic material.

20 Claims, 1 Drawing Sheet

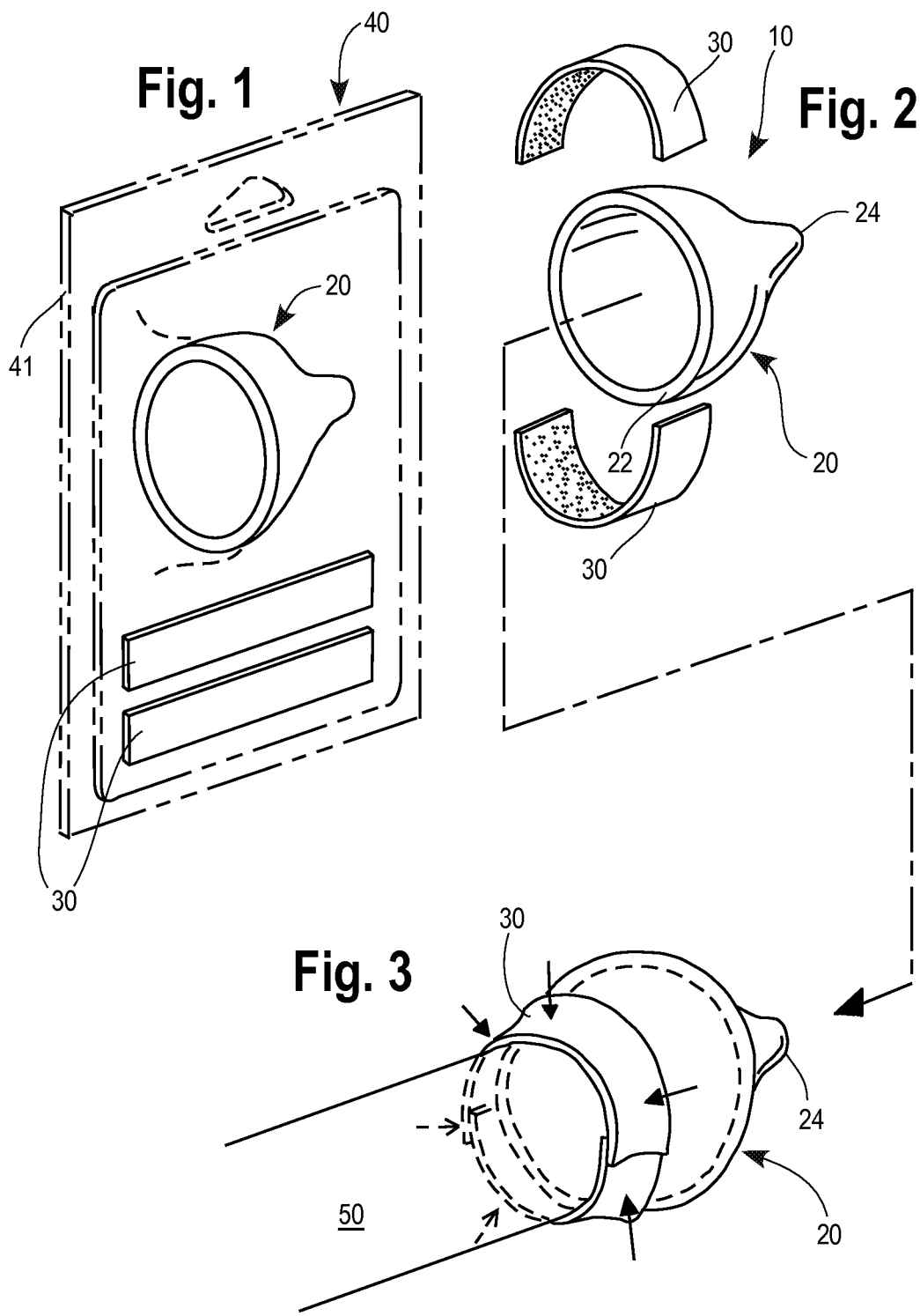

MALE CONDOM SKIN DRESSING

BACKGROUND OF THE INVENTION

The present invention generally relates to male condoms. More specifically, the invention relates to a male condom that includes a skin dressing with several advantages over prior male condoms.

The latex sheath in the early 1900s was used for sanitary purposes when covering various types of tools used during cervical exams and doctor visits. The modern condom is a combination of a sheath and a rubber ring. Similar to a balloon, the sheath is tubular in length and diameter, and is encircled by a rubber ring which is integrally molded at the base or opening of the sheath. The rubber ring primarily was designed and approved to inhibit blood flow to the male reproductive organ for the purpose of temporally lengthening erections, thus improving sexual stamina in men. The sheath, designed for its sanitary and protective capabilities, may be thinner than the ring. The sheath is still a barrier to skin-skin interaction, inhibits heat flow, and also provides less sensitivity and stimulation than skin-skin contact, which can interfere with greater control over the sexual orgasm and overall sexual performance for men.

Condom art has traditionally overlooked the stress and pressure placed on the shaft of the penis by the sheath due to its air-tight construction and non-slip adhesion. Additionally, the sheath must withstand the increased friction of rapid thrusting needed to achieve feeling and performance during intercourse. As a result, the condom can be stretched beyond capacity, and the integrity of the sheath may be compromised (torn) during sexual activity, or it may be removed altogether due to sexual frustration based on the lack of direct skin-skin contact.

Such sexual frustration can be caused by the indirect contact of the condom, which prevents direct skin contact over most or the entire length of the penis during intercourse. The result is often disconnect between partners. It creates an injustice to loving intimacy between spouses as it is one of the most widely-used methods of birth control. This problem has not been adequately addressed by the condom art.

Another prior art condom is known that is similar in nature, but which has a latex tip or hood covering designed to only cover the front tip of the male penis, as disclosed in U.S. Pat. No. 5,102,405, incorporated herein by reference. This type of "hooded" condom is designed to be unrolled and may cover only the tip or the entire length of the penis. The hood is two pieces, inner and outer portions; after the condom hood is unrolled, the outer portion is coated with a release layer and an adhesive, and can be pulled loose and discarded, leaving the inner portion on the penis.

Condom sheaths are often lubricated to facilitate the frictional contact of sexual activity. Applying lubricant to a condom as part of an application process using an adhesive can be a difficult process.

Adhesive dressings for application to skin wounds or skin infections are also known, as disclosed in U.S. Patent Application No. 20080312574, the entirety of which is hereby incorporated by reference herein.

In addition to solving the above-mentioned problems, there is also a need to provide a male condom which is easy to use, and which provides safety, uncompromising integrity and corresponding enhanced seminal security, and enhanced sexual pleasure, but which can be easily removed following sexual activity.

SUMMARY OF THE INVENTION

The objects mentioned above, as well as other objects, are solved by the present invention, which overcomes disadvantages of prior male condoms, while providing new advantages not previously associated with them.

In a preferred embodiment of the invention, a male condom skin dressing is provided, which may include a waterproof, generally conically-shaped shell having a base portion and a tip portion. The tip portion of the shell is designed to cover at least the tip of the penis. Securing material may be circumferentially wrapped around at least the base portion of the shell to aid in releasably securing the shell to the penis, while leaving a majority of the length of the penis uncovered. The securing material may include one or more flexible adhesive strips, such as one or more one-sided adhesive strips, or may include an elastic material, such as an elastic ribbon or band of rubber.

In one preferred embodiment, the securing material covers at least the tip of the penis and adjacent skin area of the penis. In another preferred embodiment, the securing material covers the tip of the penis and a substantially minor portion of the length of the penis. The shell may be made of any suitable material, such as materials that condoms are currently made of, such as but not limited to a latex material. The shell and/or the securing material may, but need not be, lubricated.

In one embodiment, the securing material may include two flexible adhesive strips, with a first of the adhesive strips covering the base portion of the shell, and a second of the adhesive strips overlapping a portion of the first and a portion of adjacent skin area of the penis.

The flexible adhesive strips are preferably waterproof, and may be oxygen-permeable.

A male condom skin dressing kit may also be provided. The kit may consist of a package with at least the following components: a waterproof, generally conically-shaped shell having a base portion and a tip portion, the tip portion designed to cover at least the tip of the penis; and one or more flexible adhesive strips designed to circumferentially wrap around the base portion of the shell and adjacent skin area of the penis to aid in releasably securing the base portion of the shell to the adjacent skin area while leaving a majority of the length of the penis uncovered. Adhesive strips may also be perforated, and supplied in bulk form, such as in rolls allowing the strips to be unrolled and individually dispensed using a dispensing mechanism.

A method of using a male condom skin dressing is also provided. The preferred method includes the steps of providing a waterproof, generally conically-shaped shell having a base portion and a tip portion; providing a securing material, such as an elastic, or one or more flexible adhesive strips; placing the shell over the tip of the penis; and wrapping the securing material, such as the elastic material or the one or more flexible adhesive strips, in a circumferential fashion over the base of the shell and/or over a skin area of the penis adjacent the base of the shell, to aid in releasably securing the shell over the tip of the penis, while leaving a majority of the length of the penis uncovered. After the commencement of sexual activity, the securing material may be unwrapped from the base of the shell and from the adjacent skin area, and the shell may be removed from the tip of the penis. If the securing material is two or more flexible adhesive strips, the wrapping step may include the step of wrapping a second, or further, adhesive strips in a circumferential fashion about a portion of the first, and about an adjacent skin area of the penis.

DEFINITION OF CLAIM TERMS

The terms used in the claims of the patent are intended to have their broadest meaning consistent with the requirements of law. Where alternative meanings are possible, the broadest meaning is intended. All words used in the claims are intended to be used in the normal, customary usage of grammar and the English language.

"Adhesive" means a length or strip of material designed to releasably adhere to human skin as well as to plastic materials which a condom may be made of, including but not limited to latex or other materials.

"Length of the penis" means the penile length from the base of the penis to the start of the glans penis or tip of the penis.

"Strip" means a length of flexible material that is substantially longer than it is wide.

"Tip of the penis" means the enlarged and bulbous-shaped end of the corpus spongiosum, forming the glans penis, which supports the foreskin, or prepuce.

BRIEF DESCRIPTION OF THE DRAWINGS

The novel features which are characteristic of the invention are set forth in the appended claims. The invention itself, however, together with further objects and attendant advantages thereof, can be better understood by reference to the following description taken in connection with the accompanying drawings, in which:

FIG. 1 is a front and side perspective view of one preferred embodiment of the present invention, in kit form;

FIG. 2 is a front and side perspective of a preferred embodiment of the invention; and FIG. 3 is a view similar to FIG. 2 showing a preferred embodiment of the invention as used in practice.

The components in the drawings are not necessarily to scale, emphasis instead being placed upon clearly illustrating the principles of the present invention. In the drawings, like reference numerals designate corresponding parts throughout the several views.

DETAILED DESCRIPTION OF THE PREFERRED EMBODIMENTS

Set forth below is a description of what are believed to be the preferred embodiments and/or best examples of the invention claimed. Future and present alternatives and modifications to this preferred embodiment are contemplated. Any alternatives or modifications which make insubstantial changes in function, in purpose, in structure, or in result are intended to be covered by the claims of this patent.

Referring now to FIGS. 2-3, a male condom skin dressing is generally referenced by numeral 10. In a preferred embodiment, skin dressing 10 may include shell 20 and one or more adhesive strips 30. A single wide adhesive strip 30 may be used, or several thinner strips 30 may be used, as may be desired. Shell 20 may be generally conically-shaped to fit over the tip of penis 50, and may include a base portion 22 and a tip portion 24. The shell may be made of any suitable deformable/elastic and liquid proof material, such as latex.

As a less desirable alternative to adhesive strips, aids to holding shell 20 in place could also consist of an elastic or other element wrapped tightly around base portion 22, which may but need not include adhesive.

Shell 20 may be lubricated, but it is preferably not lubricated for reasons explained below. Shell 20 may be made out of any suitable materials, including but not limited to latex or other similar materials. For reasons described below, shell 20 is of a length sufficient to cover only the tip of the penis, or perhaps in addition a minor portion of the length of the penis below the tip, but not more.

One or more adhesive strips 30 may be used to seal base portion 22 of shell 20 to the adjacent skin area of the penis, by circumferentially overlapping the strip(s) about this generally circular region. In one preferred embodiment, the adhesive strips may be made from Tegaderm Nexcare wound dressings, or similar materials, which are designed to be releasably secured to human skin, providing a waterproof, yet oxygen-permeable, barrier. Adhesive strips with adhesive on only one side of the strip are preferred, to facilitate handling. While a single strip may be used, two or more overlapping strips may also be employed, for extra protection and security.

In a particularly preferred embodiment, kit 40 may be packaged within plastic or other package 41 to conveniently include shell 20 and adhesive strips 30. Adhesive strips 30 could also be perforated, and supplied in bulk form, such as in rolls that may be unrolled and the perforated ends torn and dispensed using a dispensing mechanism such as a tape dispenser (such as, but not limited to, the familiar Scotch® tape dispenser).

Those of ordinary skill in the art will now appreciate distinct advantages of the present invention over prior art male condoms, including enhanced custom fit, pleasure and sensitivity over any other products currently available on the market. The custom fit not only offers the flexibility of the non-lubricated latex or lamb skin condoms, to contour to the individual identity of the male sexual anatomy, but also offers the user preferential discretion as to where the seal will be applied with every application. The custom pleasure of the present invention is delivered physically, visually, and offers a calming sense of satisfaction and peace of mind than is not believed to have been experienced or marketed to date. The custom sensitivity of the present invention offers "direct skin" contact for the entire length and diameter of the penis, up to the location of the seal, which an individual user can determine as the optimum location for a combination of pleasure and safety, i.e., to prevent internal bodily fluids from escaping or external bodily fluids penetrating the vital tip of the male reproductive organ during intercourse or upon withdrawal.

The skin dressing of the present invention addresses the obstruction problem with prior art sheaths, by permitting direct skin-to-skin contact over the majority of the length of the penis, providing increased friction and allowing the pressure of rapid thrusting to achieve enhanced sensitivity and satisfaction during intercourse. Pressure and friction remains over the middle and base of the penis, drawing the bulk of concentration and pressure from the front or tip where the seal is located, thus substantially improving the overall rate of success and likelihood for the skin dressing of the present invention to perform in an uncompromised fashion.

The invention thus enhances protection of the shell, by limiting its length, thereby limiting frictional forces that act on it. Further, the invention still protects against insemination, by employing flexible adhesive strips to cover the base of the shell, aiding in keeping the shell in place over the tip of the penis.

Additional instructions may be necessary when using the product to prevent pregnancy.

Those of ordinary skill in the art will appreciate that the skin dressing of the present invention may be applied whether the penis is erect or not, as it is envisioned that it will be typically employed to go over only the tip of the penis.

The above description is not intended to limit the meaning of the words used in the following claims that define the invention. Persons of ordinary skill in the art will understand that a variety of other designs still falling within the scope of the following claims may be envisioned and used. It is contemplated that these additional examples, as well as future modifications in structure, function, or result to that disclosed here, will exist that are not substantial changes to what is claimed here, and that all such insubstantial changes in what is claimed are intended to be covered by the claims.

I claim:

1. A male condom skin dressing, comprising:
   a generally conically-shaped shell having a base portion and a tip portion, the tip portion of the shell designed to cover at least a tip of the penis; and
   a composite dressing not attached to the shell prior to use, the composite dressing comprising a thin pliable film with top and bottom faces, wherein a pressure-sensitive adhesive is located on at least a portion of the bottom face of the film;
   wherein the composite dressing is circumferentially wrapped over and around at least a circumferential exterior surface of a portion of the base portion of the shell, and an adjacent portion of the penis, which may be erect or not, to aid in temporarily securing the shell to the penis while leaving a majority of the length of the penis uncovered.

2. The male condom skin dressing of claim 1, wherein the shell comprises a latex or lamb skin material.

3. The male condom skin dressing of claim 1, wherein the composite dressing comprises one or more adhesive aids, and wherein each of the one or more adhesive aids comprises a single-sided adhesive material.

4. The male condom skin dressing of claim 1, wherein the shell is not lubricated.

5. The male condom skin dressing of claim 1, wherein, following attachment of the dressing to the shell, the shell is lubricated.

6. The male condom skin dressing of claim 1, wherein the shell has a length from the base portion of the shell to the tip portion of the shell sufficient only to cover about the tip of the penis.

7. The male condom skin dressing of claim 1, wherein the shell has a length from the base portion of the shell to the tip portion of the shell sufficient only to cover about the tip of the penis and a substantially minor portion of the length of the penis.

8. The male condom skin dressing of claim 1, wherein the composite dressing comprises a primary exterior application in which the dressing fastens to the shell, circumferentially covering at least a portion of the base portion of the shell, and adjacent skin area of the penis.

9. The male condom skin dressing of claim 8, wherein multiple applications of the composite dressing may be applied in the user's discretion.

10. The male condom skin dressing of claim 1, wherein the shell and the adhesive dressing are each waterproof, providing a condom with a releasable waterproof seal.

11. The male condom skin dressing of claim 1, wherein the adhesive dressing is oxygen-permeable.

12. The male condom skin dressing of claim 1, wherein the adhesive dressing comprises one or more adhesive aids supplied in bulk form with perforated edges which may be torn to provide individual adhesive aids, using a separately-sold dispensing mechanism.

13. The male condom skin dressing of claim 1, wherein the adhesive a dressing comprises waterproof wound dressings.

14. The male condom skin dressing of claim 1, wherein the adhesive dressing is transparent.

15. The male condom skin dressing of claim 1, wherein the location of the adhesive dressing adjacent the base portion of the shell may be varied in the discretion of the user.

16. A male condom skin dressing kit, comprising:
   a waterproof, generally conically-shaped shell having a base portion and a tip portion, the tip portion designed to cover at least a tip of the penis, and the base portion designed to cover less than a majority of the length of the penis shaft; and
   an adhesive dressing not attached to the shell prior to use, the dressing designed to circumferentially wrap over and around at least an exterior surface of a portion of both the base portion of the shell and an adjacent skin area of the penis, to provide a temporary, releasable attachment of the base portion of the shell to the adjacent skin area, while leaving a majority of the length of the penis uncovered;
   wherein the shell and the adhesive dressing are sold together in an individual package.

17. A method of using a male condom skin dressing, comprising the steps of:
   providing a waterproof, generally conically-shaped shell having a base portion and a tip portion;
   providing an adhesive dressing not initially attached to the shell;
   placing the shell over at least a tip of the penis;
   wrapping the adhesive dressing in a circumferential fashion over and around an exterior surface of at least a portion of the base portion of the shell and over a skin area of the penis adjacent the base portion of the shell, to aid in temporarily securing the shell over the tip of the penis, while leaving a majority of the length of the penis uncovered.

18. The method of claim 17, further comprising the step, following sexual activity and withdrawal amid climax, of compressing a constrained amount of seminal fluid against the base portion of the shell, and removing the shell from the tip of the penis.

19. The method of claim 17, wherein the adhesive dressing comprises two or more adhesive strips, and wherein the wrapping step includes wrapping a second of the adhesive strips in a circumferential fashion about an exterior portion of the first.

20. The method of claim 17, further comprising the steps of providing the adhesive dressing in bulk form with perforated edges, and tearing the adhesive dressing at the perforated edges using a dispensing mechanism to provide individual flexible adhesive strips.

* * * * *